(12) United States Patent
Wilkinson

(10) Patent No.: US 8,726,915 B1
(45) Date of Patent: *May 20, 2014

(54) TOOTHBRUSH AND FLOSSING SYSTEM

(76) Inventor: William T. Wilkinson, Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/221,960

(22) Filed: Aug. 31, 2011

Related U.S. Application Data

(63) Continuation of application No. 10/973,784, filed on Oct. 26, 2004, now Pat. No. 8,015,982.

(51) Int. Cl.
*A45D 44/18* (2006.01)
*A46B 11/00* (2006.01)

(52) U.S. Cl.
USPC .......................................... 132/309; 132/311

(58) Field of Classification Search
USPC .................. 132/308–311; 15/167.1
See application file for complete search history.

(56) References Cited

U.S. PATENT DOCUMENTS

| | | | | |
|---|---|---|---|---|
| 1,312,896 A * | 8/1919 | Donnelly | ....................... | 132/309 |
| 1,646,082 A * | 10/1927 | Dailey | .......................... | 132/309 |
| 1,773,041 A * | 8/1930 | Healy | ............................ | 132/311 |
| 2,233,522 A * | 3/1941 | Fickle | ........................... | 132/309 |
| 3,480,190 A * | 11/1969 | Hyman | .......................... | 225/33 |
| 4,821,752 A * | 4/1989 | Widlak | .......................... | 132/309 |
| 8,015,982 B2 * | 9/2011 | Wilkinson | .................... | 132/309 |
| 2002/0124864 A1 * | 9/2002 | Gross et al. | ................... | 132/311 |

* cited by examiner

*Primary Examiner* — Robyn Doan
(74) *Attorney, Agent, or Firm* — Andrew L. Salvatore, Esquire

(57) ABSTRACT

A toothbrush and flossing system comprising a toothbrush having bristles, a handle, and a removable floss cartridge/container. The handle may comprise a cavity for receiving the floss cartridge; the floss container may comprise all or a portion of the handle; or the floss container may slip externally over the toothbrush handle. The floss cartridge may comprise a housing having a closed end and an open end, with a cap adapted to seal the open end and to protrude from the housing and the cavity with a recessed cutter separated from a floss exit opening in the cap. The cap may have a decorative design, such as in the form of a human, animal, cartoon character, or the like. In another embodiment, an ornamental enclosure is provided that attaches to the handle. Toothbrush embodiments for receiving the floss cartridge and floss cartridge embodiments for use with such toothbrushes are also claimed.

3 Claims, 6 Drawing Sheets

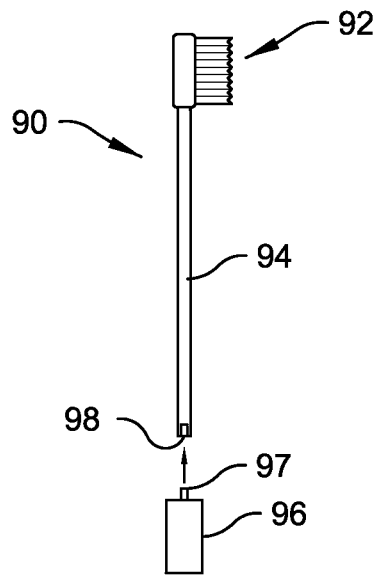
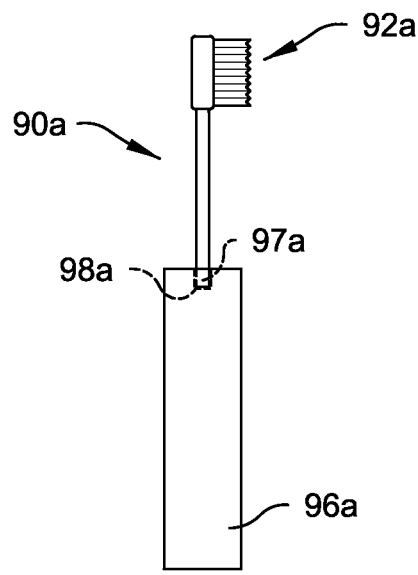
*Fig. 9A*    *Fig. 9B*
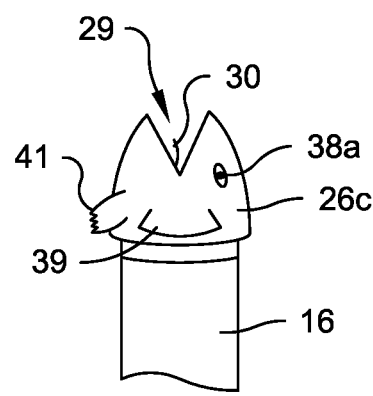
*Fig. 11*

TOOTHBRUSH AND FLOSSING SYSTEM

CROSS REFERENCE TO RELATED APPLICATIONS

This application is a continuation of, and claims priority to, U.S. patent application Ser. No. 10/973,784 filed Oct. 26, 2004. The above referenced prior application is hereby incorporated herein by reference.

FIELD OF THE INVENTION

This invention relates to dental hygiene products, specifically toothbrushes and flossing systems.

BACKGROUND OF THE INVENTION

It is generally recognized that brushing and flossing are two of the most important activities for good dental care. The American Dental Association (ADA) recommends brushing one's teeth twice a day and cleaning between the teeth with floss or interdental cleaners once each day to remove plaque from all tooth surfaces. According to an ADA study in 2003, 94% of Americans say they brush nightly; 81% say they brush first thing in the morning. It has been reported that 28% percent of Americans say they floss daily. (http://www.dentalgentlecare.com/fun_dental_facts.htm). Therefore, most people generally do not floss as frequently as they brush. One reason for this may be that the toothbrush and the floss container are typically separate, distinct units. Although a number of references discuss combination floss and toothbrush containers, it is desirable to provide a system that optimally combines the toothbrush with the floss container.

SUMMARY OF THE INVENTION

One aspect of the invention comprises a toothbrush and flossing system comprising a toothbrush having a handle with a first end and second end, a set of bristles at the first end, a cavity in handle open to the second end, and a removable floss cartridge sized to fit within the cavity and containing floss, the floss cartridge comprising an attached cap sized to seal the cavity, the cap comprising a cutter and a floss exit opening spaced from the cutter. The cutter may be recessed. The floss cartridge cap may be sized to protrude from the cavity a sufficient distance in an inserted configuration for a user to remove the cartridge by grasping the cap and pulling the cartridge out. The cutter is preferably separated from the floss exit a sufficient distance to provide a graspable length of floss between the floss exit and the cutter. In one embodiment, the floss cartridge may comprise a housing having a closed end and an open end, the floss contained within the housing, and a cap adapted to seal the open end of the housing. In one embodiment, the cartridge may comprise a rotatable spool on which the floss is wound. In another embodiment, the floss may be wound around a non-rotatable post. In still another embodiment, the floss may not be wound around any central structure at all.

The floss cartridge cap may have a non-decorative or a decorative design, such as in the form of an animal, a cartoon or licensed character, a human or humanoid form, or a seasonal theme. The cap may comprise a wedge-shaped recess within which the cutter is mounted, which in a decorative design may define a mouthlike portion of the decorative design. The floss exit opening may define an eyelike portion of the decorative design.

The floss cartridge housing closed end may comprise an axial protrusion adapted to receive an end of the spool and adapted to interface with a mating aperture within the toothbrush handle cavity. In one embodiment, the housing may have a first diameter throughout a majority of its length, an intermediate diameter for creating a force fit inside the handle cavity, and a maximum diameter for creating a force fit with the cap. In another embodiment, the housing may have a first diameter throughout a majority of its length and a maximum diameter for creating a force fit with the cap, wherein the cap comprises a lip adapted to snugly fit over an outer periphery of the handle. The handle bottom may further comprise an outer ring, wherein the cap lip comprises an inner groove adapted to receive the outer ring.

Another aspect of the invention comprises a toothbrush having a upper end and lower end, a set of bristles at the upper end, and a handle portion having a cavity axially disposed therein and open to the lower end. The toothbrush handle cavity is adapted to accept a removable floss cartridge having an integral cap that provides a closure for the cavity, the toothbrush having no other end cap attached thereto for closing the cavity. The cavity may further comprise a recess adapted to receive a protrusion on upper end of the floss cartridge.

Still another aspect of the invention comprises a removable floss cartridge sized to interface with a toothbrush having a handle with a cavity axially disposed therein and open to the lower end for receiving the cartridge, the cartridge comprising a cap sized to protrude from the toothbrush handle cavity a sufficient distance in an inserted configuration for a user to remove the cartridge by grasping the cap and pulling the cartridge out. The cap also comprises a recessed cutter separated from a floss exit opening in the cap. The floss cartridge cap may have an ornamental design, as described herein.

Yet another aspect of the invention comprises a toothbrush and flossing system comprising a toothbrush having bristles, a handle, a cavity within the handle; a detachable floss cartridge adapted to fit within the cavity; and a removable closure for covering the cavity in the toothbrush handle. The closure comprises an ornamental design selected from a group consisting of: animals, cartoon and licensed characters, humans and humanoids, seasonal themes, plants, food, and toys. The floss cartridge housing may be retained loosely within the toothbrush handle or may have a flared end that protrudes from the toothbrush handle.

Still another aspect of the invention comprises a removable floss cartridge for use with a toothbrush having a handle with a cavity therein for receiving the cartridge, the floss cartridge comprising a housing having a closed end and an open end, a spool for fitting within the housing, and an end cap adapted to seal the open end of the housing, the cap comprising a floss exit opening therein.

Yet another aspect of the invention comprises a toothbrush and flossing system comprising a toothbrush having a brush section and a handle section, the handle section comprising a removable floss container comprising a housing having a closed end and an open end and adapted for holding floss therein, and a cap comprising a recessed cutter separated from a floss exit opening in the cap.

Another aspect of the invention comprises a toothbrush and flossing system comprising a toothbrush having a brush section and a handle section, the handle section comprising a slip-on removable floss container comprising a longitudinal passage for receiving at least a portion of the handle section therein.

BRIEF DESCRIPTION OF THE DRAWINGS

FIG. 9A is an exploded side view illustration of an exemplary toothbrush embodiment having a detachable floss holder that attaches to the handle of the toothbrush.

FIG. 9B is an assembled side view illustration of the toothbrush and floss system embodiment in which the handle of the toothbrush consists of the floss container alone.

FIG. 11 is a side view of a toothbrush and floss cartridge embodiment in which the floss cartridge cap is in the shape of a fish head.

DETAILED DESCRIPTION OF THE INVENTION

Figure 1:
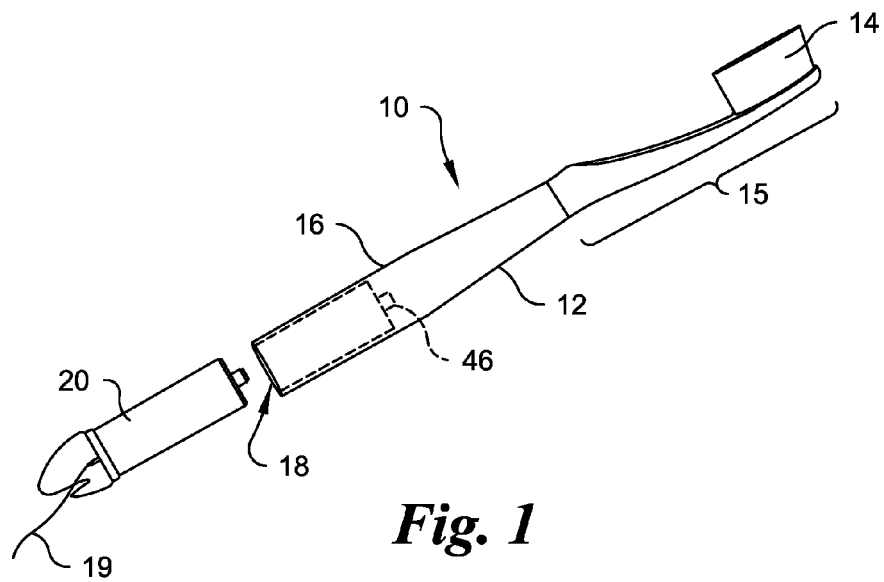
FIG. 1 is an exploded perspective view of an exemplary toothbrush embodiment with a removable floss cartridge.
Figure 2:
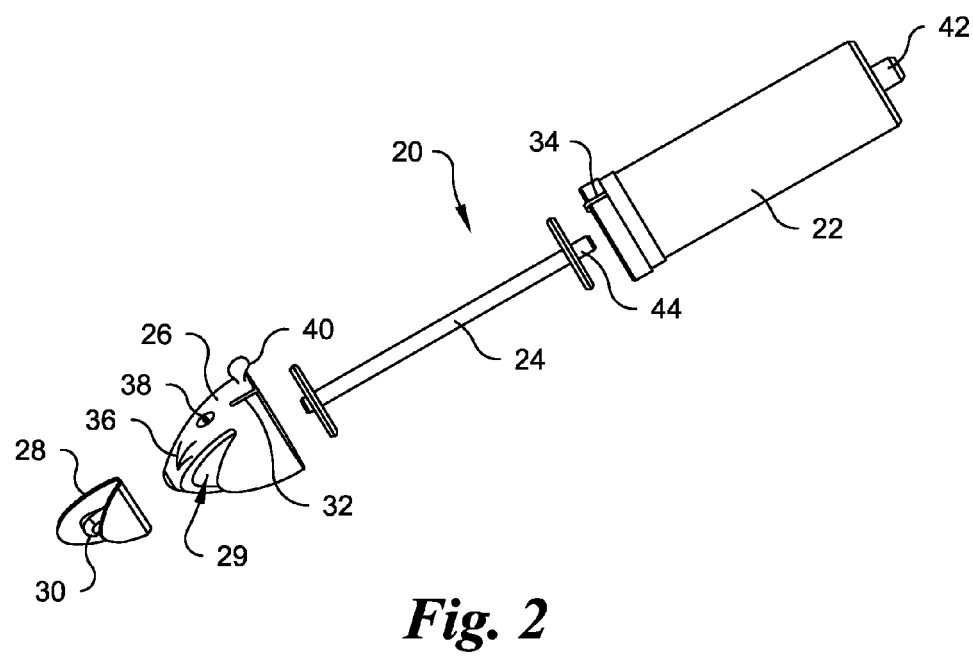
FIG. 2 is an exploded perspective detailed view of the floss cartridge of FIG. 1.
Figure 3:
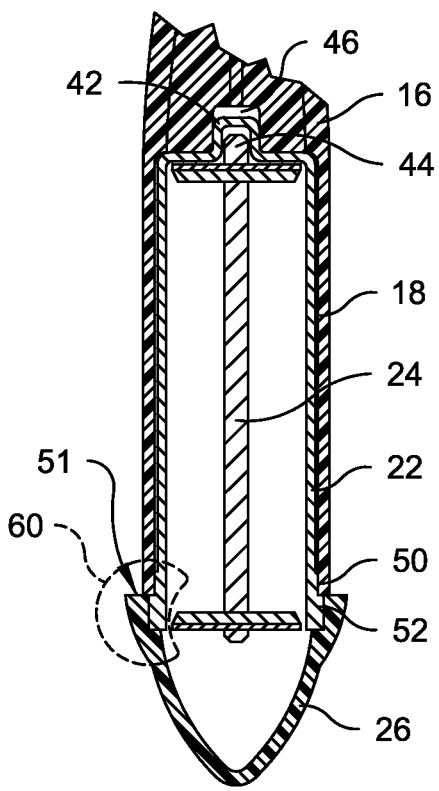
FIG. 3 is an illustration of a longitudinal sectional of the embodiment of FIG. 1, showing one cap/handle interface embodiment.

The invention will next be described with respect to the Figures. FIGS. 1-3 depict an embodiment that comprises a toothbrush/floss system design 10 comprising a toothbrush 12 having bristles 14 at an upper end for brushing the teeth and a handle 16 in which there is a hollow cavity 18 axially disposed therein and open to a lower end of the handle. Floss cartridge 20 is adapted to be inserted in cavity 18. By having a separable floss container and brush portion, the user can discard and replace the part of the system that is worn or consumed without having to discard the other portion. Upper portion 15, containing bristles 14, may be integral to handle 16 or detachable.

Referring now to FIG. 2, floss cartridge 20 comprises a housing 22, an inner spool 24 on which floss 19 (shown in FIG. 1, but omitted in FIG. 2 for better visibility of the spool) is wound, a cap 26, and a cutter insert 28. Cutter insert 28 comprises a floss cutter 30, which is typically a flap of metal into which the floss can be wedged and pulled to break the floss, as is well-known in the art. It should be understood that the term "floss" as used herein includes interdental cleaners of any type, without limitation to any particular cross-sectional shape or dimensions, including dental floss (which typically has a round cross-sectional area) and dental tape (which typically has a rectangular cross-sectional area).

The cutter is preferably recessed within the cap for safety, such as within wedge-shaped recess 29 in cap 26 as shown in the figures. Although shown with a recessed cutter, however, the cutter may also be mounted on the cap in a non-recessed configuration. Cap 26 and housing 22 each have mating slots 32 and 34, through which the floss exits the housing. Preferably, the exit aperture for the floss is spaced far enough from the cutter so that when the floss is cut, a graspable portion remains outside housing 22 to enable more floss to be pulled out. A "graspable portion" is any size portion that can be readily pinched between a user's fingers. For example, a length that is approximately the size of the average width of a human finger can be characterized as graspable. Accordingly, the graspable length for a children's toothbrush/floss system design may be smaller than for an adult system, because the size of the average child's finger is smaller than for an adult.

Cap 26, is shown in a non-ornamental form in FIG. 1, and in an ornamental form in FIGS. 2 and 11. In the ornamental form shown in FIG. 2, cap 26 has an eye 38 and whiskers 36 drawn thereon, and ears 40 formed as part of the cap, such as to make the cap resemble the head of a mouse. The design in FIG. 2 is merely a simplistic example, however, of the myriad possibilities for the floss cartridge cap. Another example can be found in FIG. 11, where the wedge-shaped recess 29 is centered along the centerline of cap 26c, which resembles a fish head, with a fin 41 formed as part of the cap and a gill cover 39 and eye 38a drawn on. The cap may typically comprise plastic or rubber, but is not limited to any particular materials, and may therefore be molded to have any ornamental design known in the art, including but not limited to designs that resemble animals, such as fish, zoo animals, insects, and the like; cartoon or other licensed characters; human or humanoids, including monsters, superheroes, aliens, celebrities, sports figures, etc.; seasonal themes, such as Santa Claus, ghosts, pumpkins, etc.; plants, such as vegetables, fruits, or flowers; toys; food; sports equipment; and the like, particularly head-like figures, much in the way that PEZ® candy dispensers have a long history of providing designs with different heads. As shown in FIGS. 2 and 11, the decorative head may be configured such that the cutter insert 28 forms a part of the mouth of the decorative head. Although shown with the floss exiting the cap through slots 32 and 34, in an alternate embodiment, eye 38 or 38a may be a exit hole for the floss.

Housing 22 is adapted to allow rotation of spool 24 therein and also to fit securely within cavity 18. Thus, as shown in FIG. 2, housing may have a protrusion 42 that is sized to receive upper end 44 of spool 24 inside and that fits into a mating aperture 46 within cavity 18. Although shown with a spool 24, other cartridge designs (exemplary embodiment of which are shown and described herein later) may omit the internal spool, opting to pack the floss directly into housing 22, or to wind the floss around a mandrel that is later removed, leaving a core-less winding, as is known in the art.

Any type of cap/handle interface (region 60 shown in FIG. 3) may be used to hold the floss cartridge 20 in place, but a pressure fit is one acceptable form. For example, as shown in FIG. 3, a longitudinal section of housing 22 shows that it has a first outer diameter throughout most of its length, but has an intermediate outer diameter section 50 adjacent the bottom of handle 16. This intermediate outer diameter section 50 when forced into cavity 18 creates a snug fit. The interface between protrusion 42 and aperture 46 also creates a snug fit. A maximum outer diameter section 52 of housing 22 receives the periphery of cap 26. As shown in FIG. 3, housing 22 is longer than cavity 18, such that maximum outer diameter section 52 of housing protrudes from the cavity when the cartridge is fully installed. Also, the cap may comprise an outer periphery that extends radially beyond handle bottom outer periphery in at least one location sufficient to create a ledge 51 of sufficient size to receive at least a user's fingernail for prying the floss cartridge from the handle bottom.

Figure 4:
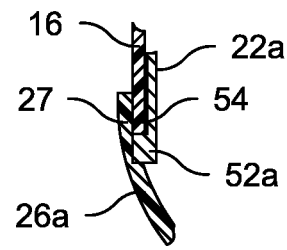
FIG. 4 is a detailed illustration of a longitudinal section of a portion of an alternate cap/handle interface embodiment.
Figure 5:
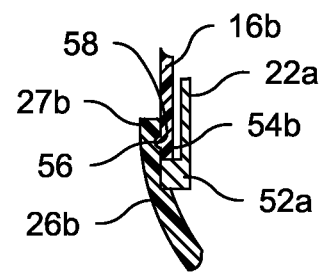
FIG. 5 is a detailed illustration of a longitudinal section of a portion of another alternate cap/handle interface embodiment.
Figure 12A:
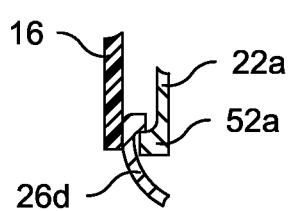
FIG. 12A is a detailed illustration of a longitudinal section of a portion of an alternate cap/handle interface embodiment, where the cap radius is smaller than the handle radius.
Figure 12B:
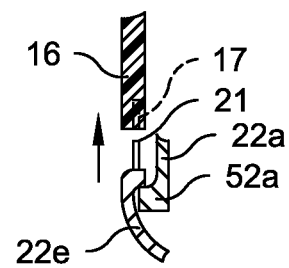
FIG. 12B is a detailed illustration of a longitudinal section of a portion of an alternate cap/handle interface embodiment, where the cap radius is equal to the handle radius.

Another cap/handle interface design, shown in FIG. 4, may comprise cap 26o being adapted to snap around the periphery of the bottom 54 of handle 16. In such an embodiment, housing 22a has a maximum outer diameter section 52a for creating a snug fit with cap 26a, but does not have an intermediate outer diameter section for creating a force fit with cavity 18. Instead, lip 27 of cap 26a extends over the bottom 54 of handle 16 to create a snug fit. In yet another embodiment, shown in FIG. 5, lip 27b of cap 26b may have an inner groove 56 adapted to receive an outer ring 58 on bottom 54b of handle 16b. The cap to handle bottom interface is not limited to any particular design. For example, although shown in FIGS. 3-5 with the cap radius greater than the handle bottom radius, the cap radius may be the same size as (such as cap 22e is shown in FIG. 12A) or smaller than (such as cap 22d is shown in FIG. 12B) the handle bottom radius. Where the cap radius is the same as the handle bottom radius, the cap may have posts 21 that interface with holes 17 in the handle to retain the cap on the handle, or the cartridge housing may have a force fit within the handle cavity, as shown in FIG. 3, omitting ledge 51 on handle 26.

Cap 26 protruding from cavity 18 and from housing 22 promotes easy removal of the cartridge. The cap-to-housing interface is typically designed to require far greater force to remove the cap (or, in the alternative, may be designed not to be removed by the consumer at all), than the force required to remove the cartridge from cavity 18. When the floss has been consumed, the floss cartridge may be replaced by a simple, two-step operation in which the old floss cartridge is removed by pulling it out (step 1) and a new refill floss cartridge is inserted by pushing it in (step 2).

Incorporating a toothbrush and floss holder in a single unit provides a number of advantages, including being more compact for storage, comprising one unit instead of two separate toothbrush and floss units. The floss cartridge provides for sanitary storage of floss, and because the brush and floss are always together, there is no need for the consumer to look for two separate units, thereby making the combined system convenient. Having the brush and floss together reminds consumers to floss at the same time as brushing, thereby encouraging better dental health. The combined design also captures sales by building brand loyalty to both the brush and the floss cartridge. Purchasing is also more convenient for the consumer, who can get both brush and floss products with a single purchase.

Where a decorative floss cartridge cap 26 is provided, the design may promote sales to collectors and may be particularly helpful for encouraging children to floss. Although the cartridges and caps may be of different colors and shapes, and may have different symbols or lettering thereon, the size and shape of the housing 22 and cavity 18 are typically standardized so that only one manufacturer's floss cartridge refill may be used with that manufacturer's brush, building brand loyalty.

Where upper portion 15 is also replaceable, different upper portions and cartridges may be made available to allow mixing and matching to allow creation of customized toothbrushes. Customization may allow users to create unique and personalized design combinations. The floss cartridge cap may be a different color than the rest of the brush, creating a distinctive two-tone look. The term "different color" means any difference perceivable to the eye of a user, including merely a difference in shade or tone of the same basic color. Similarly, the cartridge cap may have a different design than the rest of the brush—for example, the cap may have a striped design as compared to a solid color elsewhere, or the cap may have one stripe pattern as compared to a different stripe pattern in the rest of the brush. The term "design" is intended to encompass any pattern that may be present on the cap.

Providing a floss cartridge as shown and described in FIGS. 1-5 has advantages over previous designs. Many previous designs, such as U.S. Pat. Nos. 1,439,279; 1,646,082; 3,853,134; and 5,950,641 show screw-off caps that must be removed before the floss cartridge is replaced or before the floss can be used. Because the end of the floss is stored outside of the handle in the embodiments shown in FIGS. 1-5, there is no detachable cap that can be lost or that has to be removed before the user can grab the end of the floss and pull out the amount desired. By making the fit of the cap to the housing tighter than the cartridge to the handle cavity, the user only needs to pull on the cap to remove the floss cartridge in a single motion.

The use of an ornamental end unit (cap 26) as a cover for a floss cartridge, however, is not limited to the embodiment shown in FIG. 2. An alternative toothbrush design, shown in FIG. 6, may comprise a handle 60, having bristles 62, and cavity 64 for accepting a floss cartridge 66. Floss cartridge 66 may fit loosely within cavity 64 as shown in FIG. 7A, or may be force fit within the cavity and have a flared end 67 that protrudes from the cavity to allow removal of the cartridge, as shown in FIG. 7B. A removable, ornamental closure 68 is attached to handle 60 via a retaining member 69 comprising a ring 70 that fits in a mating groove 72 in the handle. Ornamental closure is functional, in that it provides a cover for the end of cavity 64 over cartridge 66, but may comprise any ornamental design, in particular, headlike designs that resemble animals, cartoons, etc., as described above with respect to FIG. 2.

Figure 6:
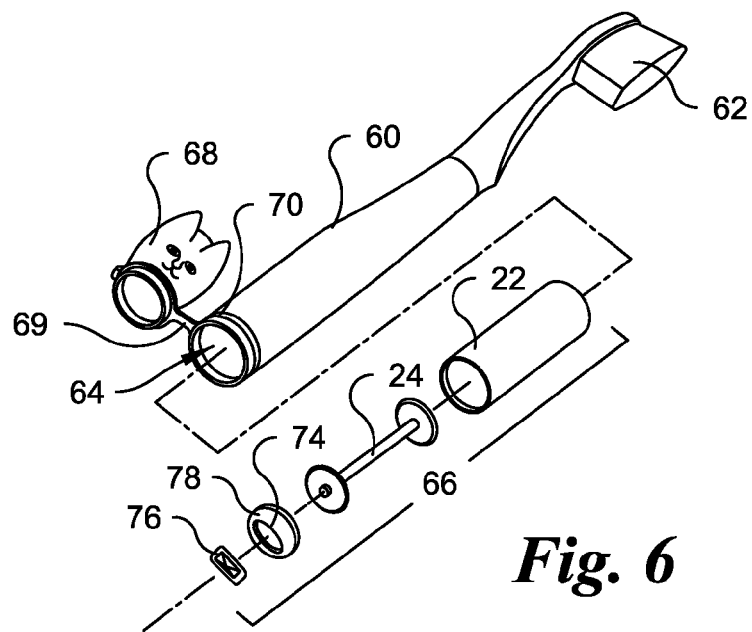
FIG. 6 is an exploded perspective view of a toothbrush embodiment in having a removable ornamental head attached to the brush handle.
Figure 7A:
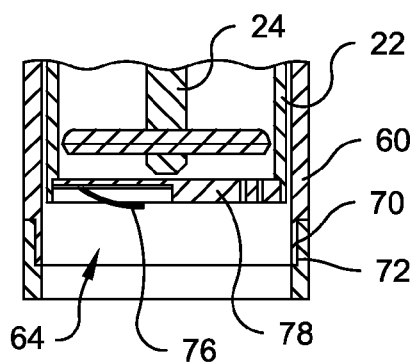
FIG. 7A is a longitudinal-section illustration of an exemplary interface between the floss cartridge and handle for the embodiment shown in FIG. 6.
Figure 7B:
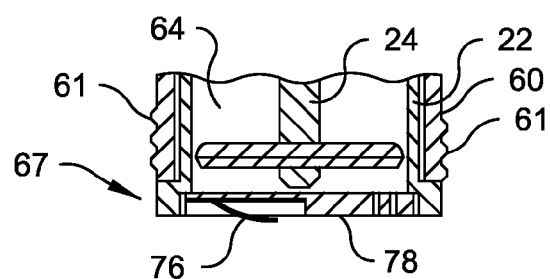
FIG. 7B is a longitudinal-section illustration of an exemplary alternate floss cartridge/handle interface for an embodiment similar to that shown in FIG. 6, but in which the cartridge has a flared end and the handle has a threaded end for receiving a screw-on/screw-off closure.

In another embodiment, shown in FIG. 7B, rather than being a snap-on ornamental closure as shown in FIG. 6, handle 60 may have external threads 61 and a corresponding closure (not shown) having mating internal threads. One advantage of providing the ring 70 to hold closure 68 on the handle as shown in FIG. 7A is that the closure is not as easily separated from the brush and lost.

Floss cartridge 66 has a floss exit opening 74 and cutter 76 on its end cap 78. In an alternate embodiment (not shown) end cap 78 may have only the floss exit hole 74, and the cutter may be provided on the ornamental closure, similar to the arrangement shown in FIG. 2. As shown in FIG. 6, the spool 24 and housing 22 may be similar to those shown in more detail in FIGS. 1-3, or of any design known in the art.

Although the embodiments shown in FIGS. 6-7B require removal of the ornamental head to replace the floss cartridge, which adds a step over the embodiments shown in FIGS. 1-5, these embodiments do have the advantage of the ornamental head being attached to the toothbrush rather than to the floss cartridge, making the replacement cost of floss cartridges less expensive than when the decorative design is integrated into the floss cartridge end cap.

Figure 10A:
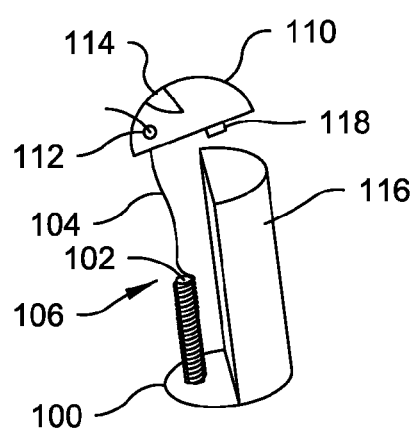
FIG. 10A is a perspective view of an exemplary floss cartridge embodiment having a non-rotatable post for holding the floss.

The preceding embodiments have depicted the floss cartridge as comprising a housing with a rotatable spool therein. The invention is not limited to such embodiments, however. As shown in FIG. I0A, floss 104 may be wound on a non-rotatable post 102 attached to a base 100, the post having an open terminal end 106 off of which the floss is adapted to unravel without any need for the base and post to turn, and without need for a housing. Cap 110, having floss exit hole 112 and recessed cutter 114, is attached to a column 116. As shown in FIG. 10A, column 116 has a semicircular cross-section and has a slot (not shown) adapted to receive a tab 118 on cap 110. Although shown with a single column 116 having a semi-circular cross section, and post 102 positioned off-center on the base, the floss cartridge is not limited to any particular number of columns, cross-section of columns, or location of columns or post. The cap may interface with the toothbrush handle in any way, such as a snug overlapping fit (similar to that shown in FIG. 4) or a groove/ring interface shown in FIG. 5, or the like.

In another cartridge embodiment, shown in FIG. I0B, spool 120 may be rotatable, but may have a base 122 and a central core 124 with a terminal end 126. Cap 128 has a recess 130 for receiving the terminal end 126 of core 124. This spool may fit within a housing, similar to the design shown and described and shown in U.S. Pat. Nos. 5,566,872 and 5,607,050, both to Dolan et al., and both incorporated herein by reference. Unlike the flip-top cap design shown in those patents, however, the cap may comprise an ornamental, protruding cap, of the type previously described and depicted herein, and the housing may be adapted to fit within a cavity in a toothbrush handle as described herein above or to otherwise comprise a portion of a toothbrush handle as described herein later. Spool 120 may fit inside a housing as shown in previous embodiments, in which case cap 128 may interface with the housing in any way shown or described herein, including a snap fit or screw top.

Figure 10B:
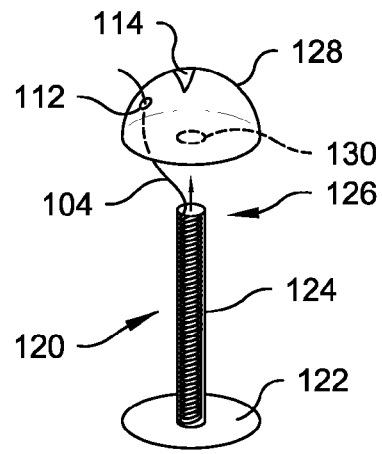
FIG. 10B is a perspective view of another exemplary floss cartridge embodiment having a spool with a terminal end that interfaces with the closure.
Figure 10C:
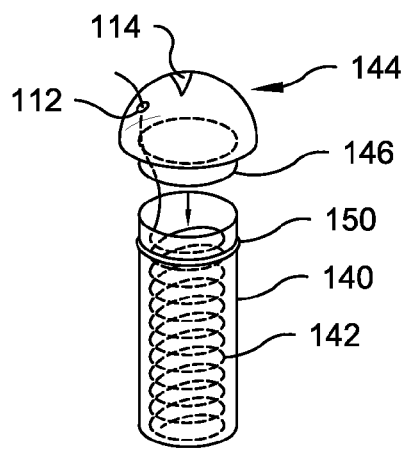
FIG. 10C is a perspective view of yet another exemplary floss cartridge embodiment, in which the floss is packed or coiled within a housing, with no central support.

In yet another cartridge embodiment, shown in FIG. 10C, the cartridge may comprise a housing 140 in which the floss 142 is coiled or packed, with no central structure about which the floss is wound. Cap 144 may have an inner ring 146 having a smaller diameter than the outer diameter of the cap, and extending into the housing, for retaining the cap within housing 140. The cap may snap fit onto the housing, for example, if the housing has an inner protrusion and the cap has a groove for receiving such protrusion. In still another design, the floss may be wound onto a central mandrel that is removed after the floss is wound around it, leaving a cylindrical winding of floss with no central supporting core.

Figure 10D:
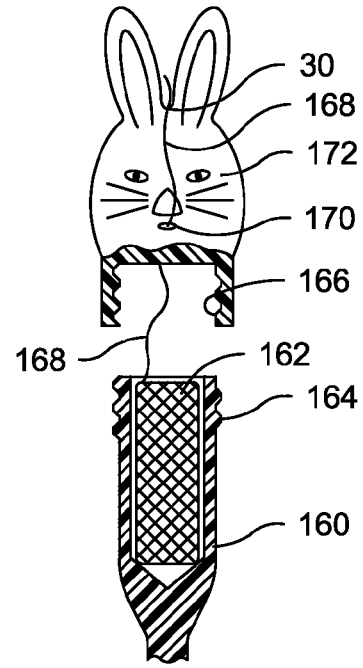
FIG. 10D is a partial cross sectional view of a toothbrush handle embodiment in which there is no structure inside the handle cavity for receiving the floss.

FIG. 10D is a partial cutaway view depicting an embodiment in which the floss cartridge 162 (shown in plan view) consists of nothing more than a winding of floss, which in other embodiments may optionally have a central core on which the floss is wound, but essentially has no structural support external to the floss. FIG. 10D also shows an embodiment in which ornamental closure 172 has a seasonal design (the Easter Bunny) with internal threads 166 for screwing the closure onto external threads 164 in handle 160. The ornamental head of the bunny comprises a mouth hole 170 through which floss 168 extends and rests in floss cutter 30 that is located between the bunny's ears. Thus, this embodiment illustrates that the recessed floss cutter can be integrated into the ornamental closure design in ways other than as a mouth as shown in FIGS. 2 and 11, and that the floss exit hole can be integrated in ways other than as an eye hole.

In any of the cartridge embodiments comprising housing, the housing may be a force fit inside the toothbrush cavity, or may comprise a ridge 150 on the outside thereof that interfaces with a mating groove (not shown) on the inside of the toothbrush cavity. Although in all of the embodiments shown in FIGS. 10A-10C, floss exit hole 112 is shown as a distinct orifice in cap 128, the cap design is not limited to any particular embodiment, and may include an ornamental design, such as is shown in FIG. 2. Similarly, although shown with a protruding cap design, the floss cartridge embodiments shown in FIGS. 10A-10C may have flat caps as for use with a removable ornamental closure 68 as shown in FIG. 6.

Another toothbrush and floss system embodiment comprises a design in which a floss unit is attached onto the toothbrush handle, such as is shown in the embodiments depicted in FIGS. 8A-8B and 9A-9B.

Figure 8A:
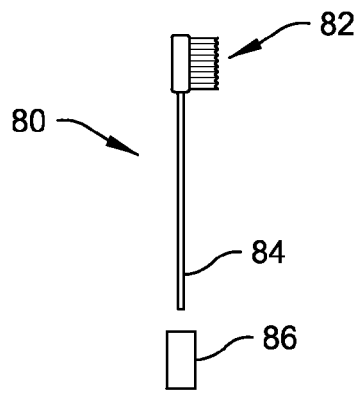
FIG. 8A is an illustration of an exemplary toothbrush embodiment having a detachable floss holder that slides onto the handle of the toothbrush.
Figure 8B:
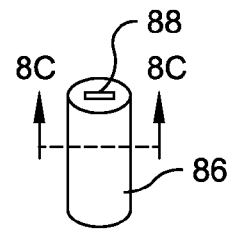
FIG. 8B is an a more detailed perspective view of the detachable floss holder of FIG. 8A.
Figure 8C:
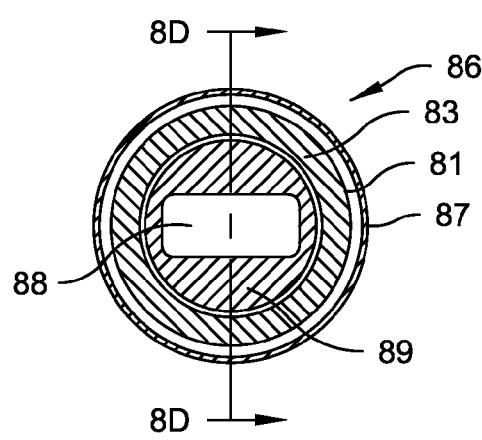
FIG. 8C is a cross-sectional view of the detachable floss holder taken along lines 8C-8C in FIG. 8B.
Figure 8D:
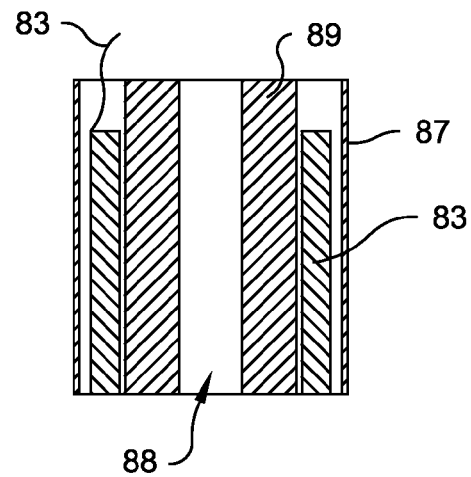
FIG. 8D is a longitudinal section view of the detachable floss holder taken along lines 8D-8D in FIG. 8C.

As shown in FIG. 8A, toothbrush 80 comprises brush section 82, handle section 84, and floss container 86 which slides onto the base of handle 84. Although the floss unit may be attached externally onto the toothbrush handle anywhere, by various attachment means such as clips, snaps, post/hole, hooks/loops, Velcro, pressure fit, and the like, in the exemplary embodiment shown in FIGS. 8A and 8B, floss unit 86 comprises a slot 88 which is sized to receive the base of handle 84 in a slip-on engagement. The interface between slot 88 and handle 84 may be relatively snug to prevent the floss container from accidentally falling off, and may include elements on the handle and within the slot to create a snap fit or a pressure fit. As shown in FIGS. 8C and 8D, floss unit 86 comprises an outer housing 87 which is connected to inner column 89 that contains slot 88. Spool 81 of floss 83 is mounted on column 89. The floss may exit housing 87 through a radial hole in housing 87, or through an opening in an end cap (not shown). Slot 88 and column 89 may extend throughout the length of housing 86, such that the end cap has an annular shape, or may only extend partially therethrough, such that the end cap may have an ornamental design of the type shown and described herein with respect to other embodiments. The end-cap to housing interface may comprise any type of interface known in the art, particularly any of the types shown or described herein.

The embodiment shown in FIG. 9A comprises toothbrush 90, having brush section 92, handle section 94, and floss container 96, in which the floss container comprises a post 97 that snap fits inside recess 98 within handle 94. The floss unit may be attached to the base of the handle by any type of attachment, including but not limited to screw-on, post/hole, twist-lock, and the like. In the embodiment shown in FIG. 9B, floss container 96a comprises the entire handle section, brush section 92a attaches directly to the floss container to form the entire toothbrush assembly 90a. In such an embodiment, it may be the floss container that has a longer life expectancy than the toothbrush bristles, in which case brush section 92a is the portion more frequently purchased as a replacement part or refill. Nonetheless, to the extent that the floss container and bristles may be on different replacement schedules, the ease of detachment of the two parts allows the user to purchase and replace either section as it becomes worn or depleted. Although not shown with a decorative cap in FIG. 9B, floss containers 96a may have ornamental cap designs similar to those shown and described herein. The interface between brush section 92a and floss container 96a may comprise a post 97*a* on the brush section 92*a* and a hole 98*a* in the container, or vice versa, with the post and hole optionally threaded to provide screw-on/screw-off functionality.

In both the embodiments shown in FIGS. 8A-8B and 9A-9B, the consumer can easily replace the floss unit by merely detaching it from the handle and attaching a new one.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A toothbrush and flossing system comprising a toothbrush having a handle with a first end and second end, a set of bristles at the first end, a cavity in the handle open to the second end, and a removable floss cartridge containing floss sized to fit within the cavity, the floss cartridge comprising an attached cap sized to seal the cavity, the cap comprising a recessed cutter, a floss exit opening spaced from the cutter, and a wedge-shaped recess defined by a wall, the cutter mounted on the wall of the recess such that when a length of floss is extended from the exit opening across the recess for cutting, the wall guides the floss toward the cutter, the floss cartridge cap having an ornamental design in the nature of a head in which the wedge-shaped recess corresponds to a first feature of the head and the floss exit opening corresponds to a second feature of the head.

2. The system of claim 1, wherein the floss cartridge cap has an ornamental design.

3. The system of claim 1, wherein the cap comprises a wedge-shaped recess within which the cutter is mounted.

* * * * *